United States Patent [19]
Sodroski et al.

[11] Patent Number: 5,654,195
[45] Date of Patent: Aug. 5, 1997

[54] VECTORS EXPRESSING HYBRID VIRUSES, METHODS OF USE AND NOVEL ASSAYS

[75] Inventors: Joseph Sodroski, Medford; William A. Haseltine, Cambridge; Norman Letvin, Newton; John Li, Boston, all of Mass.

[73] Assignee: Dana-Farber Cancer Institute, Boston, Mass.

[21] Appl. No.: 268,799

[22] Filed: Jul. 1, 1994

Related U.S. Application Data

[63] Continuation of Ser. No. 887,505, May 22, 1992, abandoned

[51] Int. Cl.$^6$ ................................................. C12N 15/86
[52] U.S. Cl. ................................ 435/320.1; 435/235.1
[58] Field of Search ............................ 435/69.1, 172.1, 435/172.3, 235.1, 320.1

[56] References Cited

PUBLICATIONS

Shebata et al. "Generation and Characterization of Infectious Chemeric Clones between Human Immunodeficiency Virus Type 1 and Simian Immunodeficiency Virus from an African Green Monkey", J. Virol., vol. 64, No. 12, Dec. 1990, pp. 5861–5868.
"Monkey–Human Viral Hybrid & New Weapons in AIDS Fight", J. Cohen, Science, vol. 257, Jul. 24, 1992, p. 478.
"Generation of a Chemerica Human and Seman Immunodeficiency Virus Infectious to Monkeys Peripheral Blood Mononuclear cells", Shebata et al. J. Virol, Jul. 1991, pp. 3514–3520.
Barre–Sinoussi et al., "Isolation of a T–Lymphotropic Retrovirus from a Patient at Risk for Acquired Immune Deficiency Syndrome (AIDS)", Science 220, pp. 868–871.
Gallo et al., "Frequent Detection and Isolation of Cytopathic Retroviruses (HTLV–III) from Patients with AIDS and at Risk for AIDS", Science 224, pp. 500–503.
Haseltine et al., "Molecular Biology of the AIDS Virus 1990", Raven Press (1990) pp. 148–152.
Cohen et al., "Identification of a protein encoded by the vpu gene of HIV–1", Nature vol. 334, Aug. 1988, pp. 532–534.
Strebel et al., "A Novel Gene of HIV–1, vpu, and Its 16–Kilodalton Product", Science vol. 241, (1988), pp. 1221–1223.
Thali et al., "Characterization of a Discontinuous Human Immunodeficiency Virus Type 1 gp120 Epitope Recognized by a Broadly Reactive Neutralizing Human Monoclonal Antibody", Journal of Virology, Nov. 1991, pp. 6188–6193.
Sodroski, et al., "Location of the Trans–Activating Region on the Genome of Human T–Cell Lymphotropic Virus Type III", Science vol. 229, (1985), pp. 74–77.
Dayton et al., "The Trans–Activator Gene of the Human T–Cell Lymphotropic Virus Type III Is Required for Replication", Cell, vol. 44, (1986) pp. 941–947.

Sodroski, et al., "A second post–transcriptional trans–activator gene required for HTLV–III replication", Nature vol. 321 (1986) pp. 412–417.
Sodroski et al., "Replicative and Cytopathic Potential of HTLV–III/LAV with sor Gene Deletions", Science vol. 231, (1986) pp. 1549–1553.
Arya et al., "Trans–Activator Gene of Human T–Lymphotropic Virus Type III (HTLV–III)", Science vol. 229, (1985) pp. 69–73.
Allan et al., "Major Glycoprotein Antigens That Induce Antibodies in AIDS Patients Are Encoded by HTLV–III", Science, vol. 228, (1985) pp. 1091–1093.
Robey et al., "Characterization of Envelope and Core Structural Gene Products of HTLV–III with Sera from AIDS Patients", Science, vol. 228, (1985), pp. 593–595.
Klatzmann et al., "T–lymphocyte T4 molecule behaves as the receptor for human retrovirus LAV", Nature, vol. 312, (1984) pp. 767–768.
Dalgleish et al., "The CD4 (T4) antigen is an essential component of the receptor for the AIDS retrovirus", Nature, vol. 312, (1984) pp. 763–767.
Fisher et al., "A molecular clone of HTLV–III with biological activity", Nature, vol. 316, (1985) pp. 262–266.
Steimer et al., "Neutralization of Divergent HIV–1 Isolates by Conformation–Dependent Human Antibodies to Gp120", Science, vol. 254, (1991) pp. 105–108.
McCune et al., "Suppression of HIV Infection in AZT–Treated SCID–hu Mice", Science, vol. 247, (1990) pp. 564–566.
Posner et al., "An IgG Human Monoclonal Antibody That Reacts With HIV–1/GP120, Inhibits Virus Binding to Cells and Neutralizes Infection", The Journal of Immunology, vol. 146, (1991) pp. 4325–4332.
McDougal et al., "Binding of the Human Retrovirus HTLV–III/LAV/ARV/HIV to the CD4 (T4) Molecule: Conformation Dependence, Epitope Mapping, Antibody Inhibition, and Potential for Idotypic mimicry", The Journal of Immunology, vol. 137, (1986), pp. 2937–2944.
Gyader, et al., "Genome organization and transactivation of the human immunodeficiency virus type 2", Nature, vol. 326, (1987) pp. 662–669.
Kang et al., "Evidence for non–V3–specific neutralizing antibodies that interfere with gp120/CD4 binding in human immunodeficiency virus 1–infected humans", Proc. Natl. Acad. Sci. USA., vol. 88, (1991) pp. 6171–6175.

Primary Examiner—David Guzo
Attorney, Agent, or Firm—David G. Conlin; Ronald I. Eisenstein

[57] ABSTRACT

A vector which can be used to establish a hybrid SIV/HIV-1 virus is described. This virus can be used to infect an animal such as a monkey to establish an animal model for in vivo testing. This animal model can be used for purposes such as screening for therapeutics, adjuvants and vaccines.

19 Claims, 6 Drawing Sheets

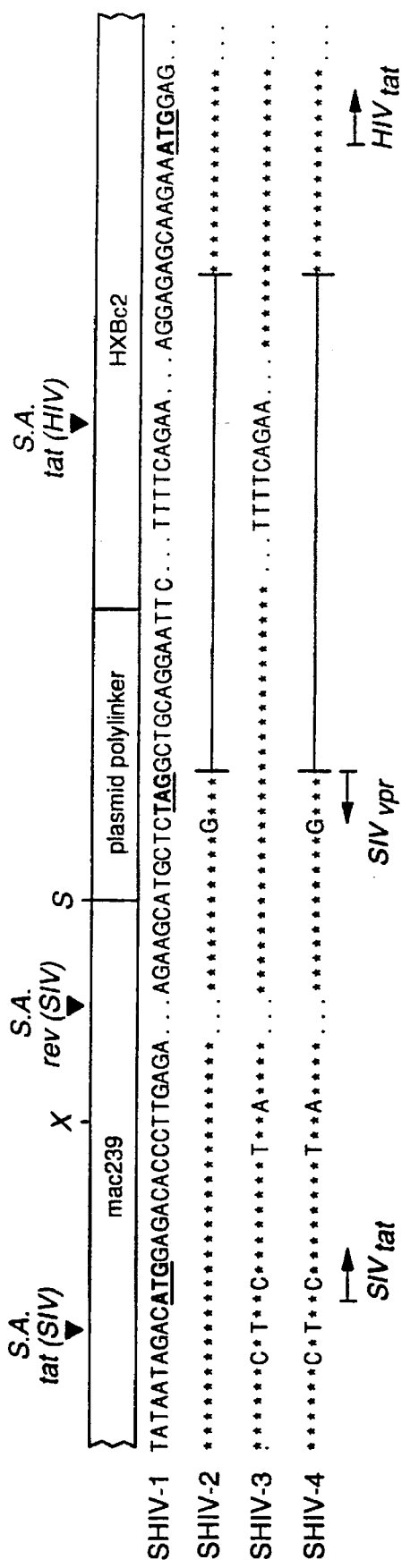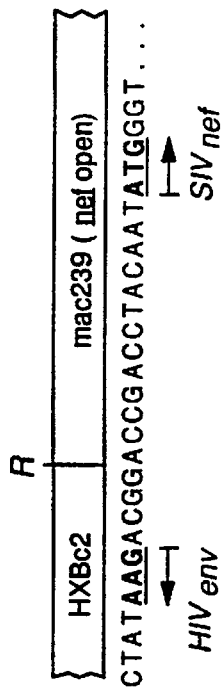
FIG. 1B
FIG. 1C

VECTORS EXPRESSING HYBRID VIRUSES, METHODS OF USE AND NOVEL ASSAYS

This is a continuation of application Ser. No. 07/887,505 filed on May 22, 1992, now abandoned.

The present invention is directed to a vector comprising a hybrid SIV/HIV genome. This vector can be used to establish an animal model for studying the HIV-1 virus.

Human immunodeficiency virus type 1 (HIV-1) and, to a lesser extent, human immunodeficiency virus type 2 (HIV-2) are etiologic agents of acquired immune deficiency syndrome (AIDS) in humans [Barre-Sinoussi, F., et al., *Science* 220:868–871 (1983); Gallo R. C., et al., *Science* 224:500–503 (1984); Clavel, F., et al., *AIDS* 1:135–140 (1987)]. These viruses are related to simian immunodeficiency viruses that infect feral populations of sooty mangabeys, African green monkeys, and mandrills [Desrosiers, R. C., et al., *Ann. Rev. Immunol.* 8:557–558 (1990)]. A simian immunodeficiency virus ($SIV_{mac}$) capable of infecting and inducing an AIDS-like disease in macaques is closely related to HIV-2 and $SIV_{smm}$ [Letvin N. L., et al., *Science* 230:71–73 (1985); Daniel M. D., et al., *Science* 228:1201–1204 (1985)].

The primate immunodeficiency viruses establish persistent infections in their hosts even in the face of an antiviral immune response. Part of this ability may reside in the capacity of these viruses to tightly regulate expression of the viral proteins, as evidenced by the presence of four conserved regulatory genes in all members of this group of retroviruses.

In addition to the gag, pro, pol and env genes typical of retroviruses, these viruses contain vif, tat, rev, and nef genes [Haseltine W., et al., *Raven Press* (1990)]. The tat protein stimulates the viral LTR to express viral RNA [Arya S., et al., *Science* 229:69–73 (1985); Sodroski J., et al., *Science* 229:74–77 (1985)] while the rev protein promotes the nuclear egress of viral messenger RNA's encoding the structural gene products [Emerman M., et al., *Cell* 57:1155–1165 (1989); Malim M., et al., *Nature* 338:254–257 (1989)]. Both tat and rev genes are essential for viral replication [Dayton A., et al., *Cell* 44:941–947 (1986); Fisher A. G., et al., *Nature* 320:367–371 (1986); Sodroski J., et al., *Nature* 321:412–417 (1986)]. The vif and nef genes, although dispensable for virus replication in some tissue culture settings, are well-conserved [Sodroski J., et al., *Science* 231:1549–1553 (1986); Fisher A. G., et al., *Science* 237:888–893 (1987); Strebel K., et al., *Nature* 328:728–730 (1987); Kestler H. W., et al., *Cell* 65:651–662 (1991)]. Depending upon the particular primate immunodeficiency virus, vpx, vpr and/or vpu genes are present in the proviral DNA [Desrosier R. C., et al., *Ann. Rev. Immunol.* 8:557–578 (1990); Haseltine W., *Raven Press* (1990)]. These genes are also dispensable for virus replication in tissue culture. The vpx and vpr proteins are incorporated into virions and are believed to play a positive role in the early phase of the virus life cycle [Cohen E. A., et al., *JAIDS* 3:11–18 (1990); Yu, X-F, et al., *J. Virol.* 64:5688–5693 (1990); Henderson L. E., et al., *Science* 241:199–201 (1988); Hu, W., et al., *Virology* 173:624–630 (1989); Kappes J. C., et al., *Virology* 184:197–209 (1991); Hattori N., et al., *Proc. Natl. Acad. Sci. U.S.A.* 87:8080–8084 (1990)]. The vpu gene is found only in HIV-1 and encodes a 15–20 kD protein, depending upon the virus isolate [Terwilliger E. F., et al., *Proc. Natl. Acad. Sci. U.S.A.* 86:5163–5167 (1989); Cohen E. A., et al., *Nature* 344:532–534 (1988); Strebel K., et al., *Science* 241:1221–1223; (1988); Klimkait T., et al., *J. Virol.* 64:621–629 (1990)]. The vpu protein is associated with the host cell membranes and facilitates the redistribution of viral proteins from inside the infected cell to free virion particles [Terwilliger E. F., et al., *Proc. Natl. Acad. Sci. U.S.A.* 86:5163–5167 (1989); Cohen E. A., et al., *Nature* 344:532–534 (1988); Strebel K., et al., *Science* 241:1221–1223; (1988); Klimkait T., et al., *J. Virol.* 64:621–629 (1990); Strebel K., et al., *J. Virol.* 63:3784–3791 (1989)]. Thus, the major function of the vpu product is to modulate virus release, although other effects of vpu on envelope glycoprotein or CD4 steady state levels have been observed [Willey R., et al., *J. Virol.* 66:226–234 (1992); Kimura T. and Karn J., personal communication]. The in vivo function of the vpu protein is unknown.

The persistence of primate immunodeficiency virus infection is also made possible by the particular features of the viral envelope glycoproteins. The viral glycoproteins are synthesized as a 160 Kd precursor, which is cleaved intracellularly to yield the gp120 exterior envelope glycoprotein and the gp41 transmembrane glycoprotein [Allan J. S., et al., *Science* 228:1091–1093 (1985); Robey W. G., et al., *Science* 228:593–595 (1985)]. The gp120 glycoprotein binds the CD4 receptor, following which the gp120 and gp41 glycoproteins in concert contribute to the membrane fusion process [Klatzmann D., et al., *Nature* 312:767–768 (1984); Dalgleish A. G., et al., *Nature* 312:763–767 (1984); Helseth E., et al., *J. Virol.* 64:2416–2420 (1990)]. The latter process mediates both virus entry and viral cytopathic effect, which consists of multinucleated giant cell (syncytium) formation and single cell lysis [Sodroski J., et al., *Nature* 322:470–474 (1986); Lifson J. D., et al., *Nature* 323:725–728 (1986); Kowalski K., et al., *J. Virol.* 65:281–291 (1991)]. The exterior envelope glycoproteins of these viruses are heavily glycosylated and contain regions of hyper-variability, most of which are thought to consist of disulfide-linked loops exposed to the exterior of the protein [Leonard C., et al., *J. Biol. Chem.* 265:10373–10382 (1990)]. In the case of HIV-1, most of the neutralizing antibody response elicited early in the course of infection is directed against the third variable (V3) loop of the gp120 glycoprotein [Nara P., et al., *Proc. Quatreime Colloque des Cent Cardes* (Girard, Valette, eds, Paris: Pasteur Vaccins) pp. 203–215 (1989)]. These antibodies inhibit some aspect of the membrane fusion process [Skinner M., et al., *J. Virol.* 62:4195–4200 (1988); Linsley P., et al., *J. Virol.* 62:3695–3702 (1988)]. Neutralization is generally strain-restricted due to variation in the V3 region, but some antibodies recognize better conserved elements near the tip of the loop [Ohno T., et al., *Proc. Natl. Acad. Sci. U.S.A.* 88:10726–10729 (1991); Matthews T., et al., *Proc Natl. Acad. Sci. U.S.A.* 83:9709–9713 (1986); Javaherian K., et al., *Science* 250:1590–1593 (1990)]. The anti-V3 loop antibodies are protective against intravenous challenge by homologous HIV-1 [Berman P., et al., *Nature* 345:622–625 (1990); Emini E., et al., *Nature* 355:728–730 (1992)]. Later in the course of HIV-1 infection, antibodies that neutralize a broader range of HIV-1 isolates are generated [Weiss R. A., et al., *Nature* 324:572–575 (1986); Profy A., et al., *J. Immunol.* 144:4641–4647 (1990); Berkower I., et al., *J. Exp. Med.* 170:1681–1695 (1989)]. These antibodies recognize discontinuous epitopes near the CD4 binding site of gp120 and block the binding of gp120 to CD4 [Ho D., et al., *J. Virol.* 65:489–493 (1991); Kang C-Y, et al., *Proc. Natl. Acad. Sci. U.S.A.* 88:6171–6175 (1991); Steimer K. S., et al., *Science* 254:105–108 (1991)]. The epitopes for some of these antibodies have been mapped by extensive mutagenesis, and depend upon amino acids located in all five conserved gp120 regions [Thali M., et al., *J. Virol.* 65:6188–6193 (1991); Thali M., et al., Discontinuous, conserved neutralization epitopes overlapping the CD4 binding region of the HIV-1 gp120 envelope glycoprotein, submitted]. These neutralizing antibodies do not keep virus replication in check indefinitely, probably because of virus variation and selection of neutralization-resistant viruses and because of immunosuppression and compromised ability of the host to respond to novel epitopes [Nara P., et al., *J. Virol.* 64:3779–3791 (1990); Gegerfelt A., et al., *Virology* 185:162–168 (1991); Arendrup M., et al., *JAIDS* 5:303–307 (1992)]. It is critical to both immunotherapeutic and vaccine efforts that an understanding of neutralizing antibodies and virus variation as a means of escape is achieved.

A major tool in vaccine efforts is an animal model in which variables related to immunization protocols, adjuvant choice, virus challenge strain, state of the virus (cell-free versus cell-associated) and mode of challenge (mucosal versus intravenous) can be assessed. In the HIV-1 system, many of these variables have not been suitably addressed due to the scarcity and expense of the chimpanzees required. The chimpanzee model is of limited utility for immunotherapeutic efforts since the level of HIV-1 replication is variable and, to date, little evidence of disease induction exists [Fultz P., et al., *Science* 226:549–552 (1986)]. HIV-1 infection of mice, rabbits and SCID-hu mice has been reported [McCune J., et al., *Science* 247:564–566 (1990); Mosier D., et al., *Science*,251:791–794 (1991); Filice G., et al., *Nature* 335:366–369 (1988)], but the applicability of these models for vaccine and immunotherapeutic efforts remains questionable.

The most useful current model for HIV infection is the infection of macaques with various strains of $SIV_{smm}$, $SIV_{mac}$, or HIV-2 [Desrosier R. C. et al., *Ann. Rev. Immunol.* 8:557–578 (1990); Letvin N. L. et al., *Science* 230:71–73 (1985)]. AIDS-like diseases have been induced using infectious molecular clones of $SIV_{mac}$, and recently an animal-passaged HIV-2 has been reported to induce disease in cynomolgus monkeys [Biberfeld G., et al., *Sixieme Colloque des Cent Cardes* (eds., Girard, Valette, Paris, Pasteur Vaccins), pp. 225–229 (1991)]. The availability of these monkeys has allowed many more experimental variables relevant to vaccine development or genetic variation to be tested, relative to the HIV-1/chimpanzee model. Although the contribution of human cell components to protection has recently clouded interpretation of some of the vaccine results using the SIV/macaque model [Scott E. J. et al., *Nature* 353:393 (1991)], it does appear that priming with vaccinia/$gp160_{SIV}$ followed by boosting with purified SIV gp120 can confer protection against the homologous virus [Hu S. L., et al., *Science* 255:456–459 (1992)]. Also, the in vivo role of the nef gene of SIV in contributing to virus replication was demonstrated using this system [Kestler H. W., et al., *Cells* 65:651–662 (1991)]. While relevant to primate immunodeficiency viruses in general and relevant to HIV-2 in particular, it has limitations with respect to HIV-1, specifically.

As a greater understanding of the molecular details of the antiviral immune response to the primate immunodeficiency viruses emerges, it is becoming increasingly clear that significant differences exist between the envelope glycoproteins of HIV-1 and those of the HIV-2/$SIV_{smm}$ viruses. While general organizational features of these glycoproteins are conserved among the primate immunodeficiency viruses, structural differences exist in the number of disulfide bonds, the particular amino acids near or within the CD4 binding region or gp41 amino terminal fusion peptide, and the composition of the hypervariable loops [Myers G., et al., "Human retroviruses and AIDS" (1991)]. These structural differences translate into significant differences in the immune responses generated to the HIV-1 and HIV-2/$SIV_{smm}$ glycoproteins. Both major groups of neutralizing antibodies generated by HIV-1 do not apparently correspond to those elicited by the HIV-2/$SIV_{smm}$ viruses. The V3 loop of HIV-1 is exposed on the native glycoprotein, efficiently elicits neutralizing antibodies and can determine the ability of HIV-1 to enter primary monocytes/macrophages [Ohno T., et al., *Proc. Natl. Acad. Sci. U.S.A.* 88:10726–10729 (1991); Matthews T., et al., *Proc. Natl. Acad. Sci. U.S.A.* 83:9709–9713 (1986); Javaherian K., et al., *Science* 250:1590–1593 (1990); Hwang S. S., et al., *Science* 253:71–74 (1991)]. By contrast, the analogous region of $SIV_{mac}$ is not variable, does not appear to be well-exposed on the native glycoprotein, is not an efficient target for neutralizing antibodies, and does not correspond to the region of SIV env implicated in primary macrophage tropism [Burns D. P. W., et al., *J. Virol.* 65:1843–1854 (1991); Overbaugh J., et al., *J. Virol.* 65:7025–7031 (1991); Scott Putney, personal communication; Mori K., et al., *J. Virol.* in the press (1992)]. In contrast to the broadly neutralizing antibodies of HIV-1, many of which block gp120-CD4 binding and recognize discontinuous epitopes spanning most of the conserved regions [Ho D., et al., *J. Virol*, 65:489–493 (1991); Kang C-Y, et al., *Proc. Natl. Acad. Sci. U.S.A.* 88:6171–6175 (1991); Steimer K. S., et al., *Science* 254:105–108 (1991); Thali M., et al., *J. Virol.* 65:6188–6193 (1991); Thali M., et al., Discontinuous, conserved neutralization epitopes overlapping the CD4 binding region of the HIV-1 gp120 envelope glycoprotein, submitted; Posner M., et al., *J. Immunol.* 146:4325–4332 (1991); Tilley S. A., et al., *Res Virol.* 142:247–259 (1991)], the major conserved neutralization epitope of $SIV_{mac}$ is confined to a 179 amino acid carboxyl fragment of gp120 [Javaherian K., et al., *Sixieme Colloque des Cent Gardes* (eds., Girard, Valette, Paris, Pasteur Vaccins), pp161–164 (1991)]. Although the latter epitope is discontinuous, it does not overlap the CD4 binding site, since ternary complexes of gp120, soluble CD4, and neutralizing antibody can be formed [Javaherian K., et al., *Sixieme Colloque des Cent Gardes* (eds., Girard, Valette, Paris, Pasteur Vaccins), pp161–164 (1991)]. The existence of differences between the conserved neutralization epitopes of the HIV-1 and HIV-2/$SIV_{smm}$ groups of viruses is further emphasized by the observation that broadly neutralizing monoclonal antibodies directed against these viruses do not cross-neutralize members of the other group [Weiss R. A. et al., *Nature* 324:572–575 (1986); Ho D., et al., *J. Virol.* 65:489–493 (1991); Posner M., et al., *J. Immunol.* 146:4325–5332 (1991); Tilley S. A., et al., *Res. Virol.* 142:247–259 (1991)]. Thus, we cannot expect that the details of vaccine or immunotherapeutic formulation will be directly extrapolatable from the HIV-2/$SIV_{smm}$ models to HIV-1. This, plus the absence of certain genes like vpu from the SIV genome, illustrate the need to establish new animal models that allow assessment of the in vivo consequences of variation within HIV-1-specific genes. Preferably, these models should involve both infection by the virus and disease induction.

HIV-1 has been reported to infect *Macaca nemestrina* after inoculation with cell-associated virus [Katze J., et al., personal communication, UCLA Symposium of HIV and Related Viruses, Keystone, CO (1992)]. However, to date, no disease has been reported to be observed in the infected macaques, six months after inoculation. Although the HIV-1/M-nemestrima system would have HIV-1 specific genes, it is limited to one macaque species and has not been reported to yield disease. Furthermore, *macaque nemestrima* is not widely used in primate centers in this country, so it would take considerable time, effort and expense to be able to use such species.

Shibata, R., et al. reported preparing a chimeric virus containing HIV-1 tat, rev and env genes in a SIV provirus *J. Virol.* 65:3514–3522 (1991). This SIV provirus does not contain functional vpr and nef genes. Indeed, it was reported that SIV vpr and SIV nef are not necessary for viral replication and infection of tissue cultured cells by these authors. These chimeric viruses were reported to replicate in macaque peripheral blood mononuclear cells (PBMC). The Shibeta et al. chimeric virus has been claimed to infect macaques, but the level of virus replication was very low and the infection did not persist beyond two months (Hayami, personal communication).

It would be desirable to have a vector containing HIV-1 genes which produces a virus that could be used to infect a number of animals in addition to humans and chimpanzees in order to be able to develop an animal system for studying the disease. It would also be useful if such a system was set up so that different HIV strains could readily be studied. It would also be useful if an animal model could be established so that antibody protection, virus variation and virus infection could be studied.

Still further, it would be useful to be able to use such a system for the preparation and/or screening of vaccines, therapeutics and modes of administration.

It is yet another objective of the present invention to prepare a vector into which the different envelope genes of the various HIV-1 strains can be inserted, which can then be used to infect animal models in order to prepare vaccines, prepare therapeutics and follow the evolution and differentiation of envelope glycoprotein in vivo.

All of these uses require a virus that replicates efficiently and achieves a high titer in several monkey species. Such a system is currently unavailable.

SUMMARY OF INVENTION

We have now discovered a vector which consists essentially of a DNA sequence containing a 5' portion corresponding to a sufficient number of nucleotides to encode the following functional SIV or HIV-2 structural proteins, gag, pro, pol of SIV or HIV-2, and to encode as functional SIV regulatory proteins, vif, vpx, and vpr, and having a 5' SIV or HIV-2 LTR and a 3' portion corresponding to a sufficient number of nucleotides corresponding to an HIV-1 genome to encode as a functional HIV-1 structural protein, env, and as functional HIV regulatory proteins, tat and rev and as a functional SIV or HIV-2 regulatory protein, nef, and having a SIV or HIV-2 LTR. In a preferred embodiment, the 3' portion also contains a sufficient number of nucleotides to encode a functional HIV-1 vpu gene. Preferably, the nucleotide sequence of the vector contains sequences that correspond to the SIV or HIV-2 tat splice acceptor and/or the SIV or HIV-2 rev splice acceptor, but does not contain sequences corresponding to the HIV-1 tat splice acceptor. Preferably, the SIV genome corresponds to the SIV genome of the strain $SIV_{mac}$, $SIV_{agm}$, $SIV_{MND}$. More preferably it corresponds to $SIV_{mac}$.

The HIV genome can correspond to any of the known HIV-1 strains. In one preferred embodiment, the HIV segment corresponds to HIV genomes capable of encoding functional vpu proteins such as ELI, BH10, BRU, etc.

When the HIV or SIV strain corresponds to a genome not capable of encoding a function protein such as vpu of HXBc2 strain or nef of $SIV_{mac}239$, one can modify the sequence in order to produce a sequence that will encode a functional protein. For example, with the strain HXBc2, one would modify the DNA sequence to insert an AUG codon immediately upstream and in proper reading frame with the vpu open reading frame at a nucleotide corresponding to immediately before HIV nucleotide 5541 or create a point mutation to generate such a sequence. This can readily be done by techniques well known in the art.

BRIEF DESCRIPTION OF THE DRAWINGS

FIG. 1 (Parts A–D) is a linear schematic showing the structure of one of the preferred hybrid vectors.

FIG. 1B shows the details of the 5' $SIV_{mac}$/HIV-1 junction near the Sph I site (S) SEQ ID NO:1–7 for a variety of hybrid vectors.

FIG. 1C shows the details of the 3' HIV-1/$SIV_{mac}$ 239 (nef open) junction SEQ ID NO:8 near the Rsr II site (R).

FIG. 3 shows viral protein production in cells infected by these vectors.

DETAILED DESCRIPTION OF THE INVENTION

Figure 1A:
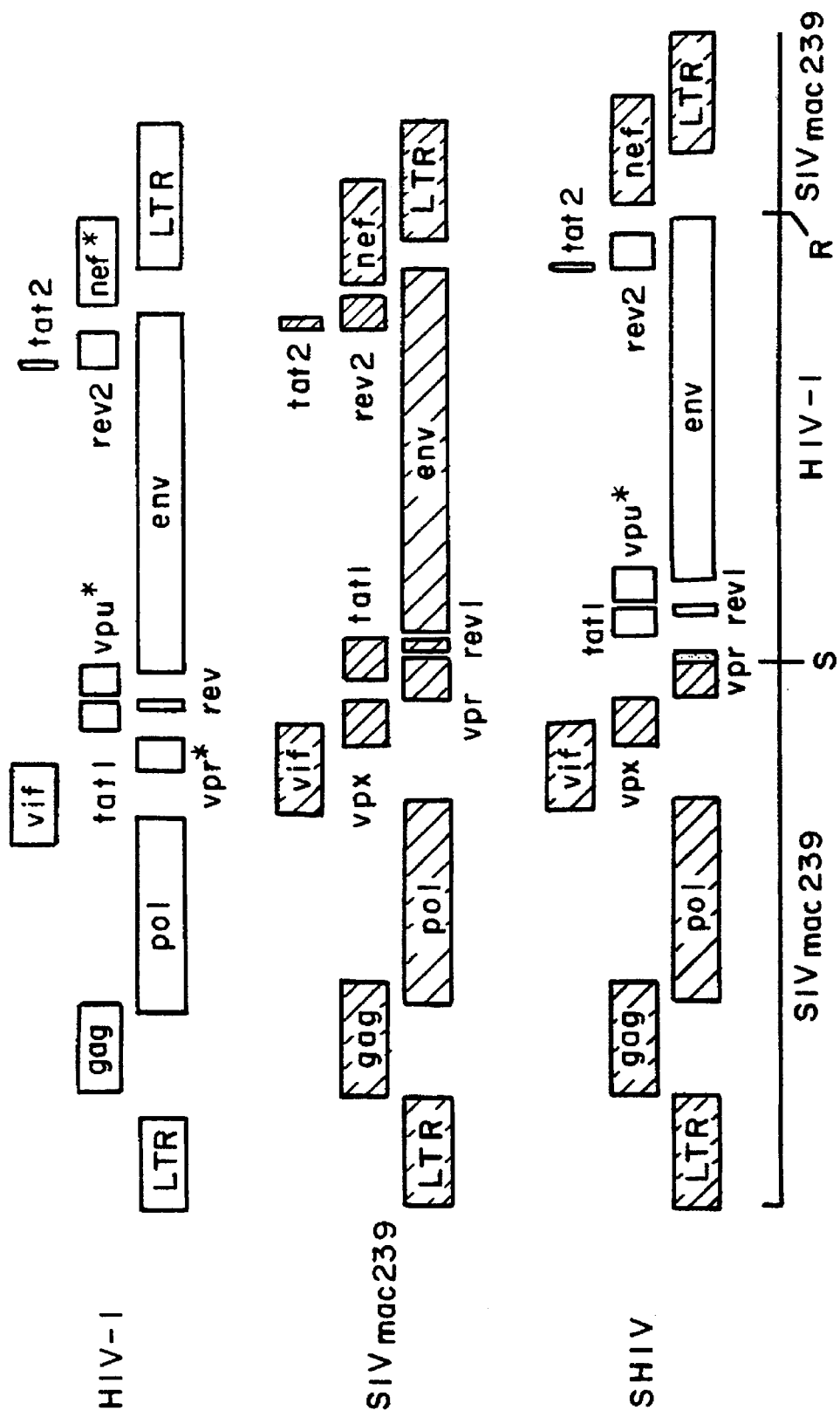
FIG. 1A is a linear schematic of the genetic organization of the HIV-1 sequence and the SIV sequence.

We have now discovered vectors that will produce chimeric viruses containing HIV-1 components. As a result of transfecting a cell with these vectors, replication competent viruses that are infectious in animal systems such as monkeys, mandrils, macaques, etc. can be produced.

The typical method of developing a vaccine to prevent infection by a virus has utilized suitable animal models. However, the two animal models most commonly used have serious deficiencies with respect to studying HIV-1. HIV-1 does not replicate to high titers in chimpanzees and infected chimpanzees do not develop immunodeficiency. [Alter, H., et al. *Science* 226:549–552 (1984); Fultz, P. N., et al., *J. Virol.* 58:116–124 (1986); Fultz, P., et al., *Science* 226:549–552 (1986); Gajdusek, D. C., et al., *Lancet* 1:55–56 (1985); and Nara, P. L., et al., *J. Virol.* 61:3173–3180 (1987)]. Furthermore, trials in chimpanzees are limited to a few animals since the species is endangered and available chimpanzees and their care is expensive.

Rhesus and cynomolgus macaque monkeys infected with SIV such as the macaque strain of SIV ($SIV_{mac}$) produce high titers of virus and develop an AIDS-like syndrome [Daniel, M. D., et al., *Science* 228:1201–1204 (1985); Kestler, *Science* 248:1109–1112 (1990); Letvin, N. L., *Science* 230:71–73 (1985)]. However, differences exist in the immune response to SIV-1 and $SIV_{mac}$ envelope glycoproteins, which represent the principal targets for protective immunity and the response to HIV-1 envelope glycoproteins. [Berman, P., et al., *Nature* 345:622–625 (1990);

Emini, E., et al., Nature 355:728–730 (1992); Hu, S. L., et al., Science 255:456–459 (1992)]. The major neutralizing antibodies in HIV-1 infected people are directed against two regions of the gp120 envelope glycoprotein. Antibodies against the HIV-1 third gp120 variable (V3 region) have been reported to be protective [Emini, E., et al. Nature, supra]. As the name implies, this region shows great sequence variation among the various HIV strains. In contrast, the corresponding region of the $SIV_{mac}$ envelope glycoprotein does not exhibit sequence variation among isolates and is not a target for neutralizing antibodies in infected macaques. [Burns, D. P. W., et al., J. Virol. 65:1843–1854 (1991); Overbaugh, J., et al., J. Virol. 65:7025–7031 (1991)]. HIV-1 infected humans also exhibit a second group of neutralizing antibodies which are directed against a conserved discontinuous gp120 region that binds the CD4 viral receptor. [Berkower, I., et al, J. Exp. Med. 170:1681–1695 (1989); Dalgleish A. G., et al. Nature 312:763–767 (1984); Haigwood, N., et al., Vaccines 90:313–320 (1990); Ho, D., et al., J. Virol. 65:489–493 (1991); Kang, C. Y., et al., Proc. Natl. Acad. Sci. U.S.A. 88:6171–6175 (1991); Klatzmann, D., et al., Nature 312:767–768 (1984); McDougal, J. S., et al., J. Immunol. 137:2937–2944 (1986); Posner, M., et al, J. Immunol. 146:4325–4332 (1991); Profy, A., et al., J. Immunol. 144:4641–4647 (1990); Steimer, K. S., Science 254:105–108 (1991); Tilley, S. A., Res. Virol. 142:247–259 (1991)].

However, this second group of antibodies recognize HIV-1 gp120 regions that are distinct from those of the $SIV_{mac}$ gp120 glycoproteins recognized by antibodies from infected macaques that neutralize multiple SIV strains. [Thali, M., et al., J. Virol. 65:6188–6193 (1991); Javaherian, K., et al., pp. 161–4 in Sixieme Colloques des Cent Dardes (Eds., M. Girard and L. Valerie, Paris, Pasteur Vaccins)]. This difference between the antibodies that broadly neutralize HIV-1 and SIV strains is further stengthened by the finding that such antibodies do not cross-neutralize. [Weiss, R. A., et al., Nature 324:572–575 (1986)].

We have found a vector which will produce a hybrid virus between HIV-1 and SIV (or HIV-2), which expresses HIV-1 envelope glycoproteins and is capable of replicating to high titers in animal systems such as monkeys, preferably macaque monkeys. As used herein the term SIV will also refer to HIV-2. $SIV_{smm}$, $SIV_{mac}$ and HIV-2 have all been used to induce disease in monkeys.

The vector consists of a DNA sequence comprising the SIV LTRs and a sufficient number of nucleotides to encode functional SIV nef protein. The SIV sequences preferably correspond to $SIV_{agm}$, $SIV_{MND}$, $SIV_{mac}$ or HIV-2. More preferably the sequences correspond to $SIV_{mac}$ or HIV-2. Still more preferably, the sequences correspond to $SIV_{mac}$. The vector also comprises a sufficient number of nucleotides corresponding to the HIV-1 genome to encode functional HIV-1 tat, rev and env proteins. The vector also contains a sufficient number of nucleotides to encode functional HIV or SIV gag, pol, pro and vif and vpr proteins. Preferably, it also encodes functional vpu and/or vpx proteins. In one preferred embodiment the vector encodes functional HIV-1 gag, pol, pro, vif, vpr, vpu, env, rev and tat proteins, and functional SIV nef protein.

Figure 1D:
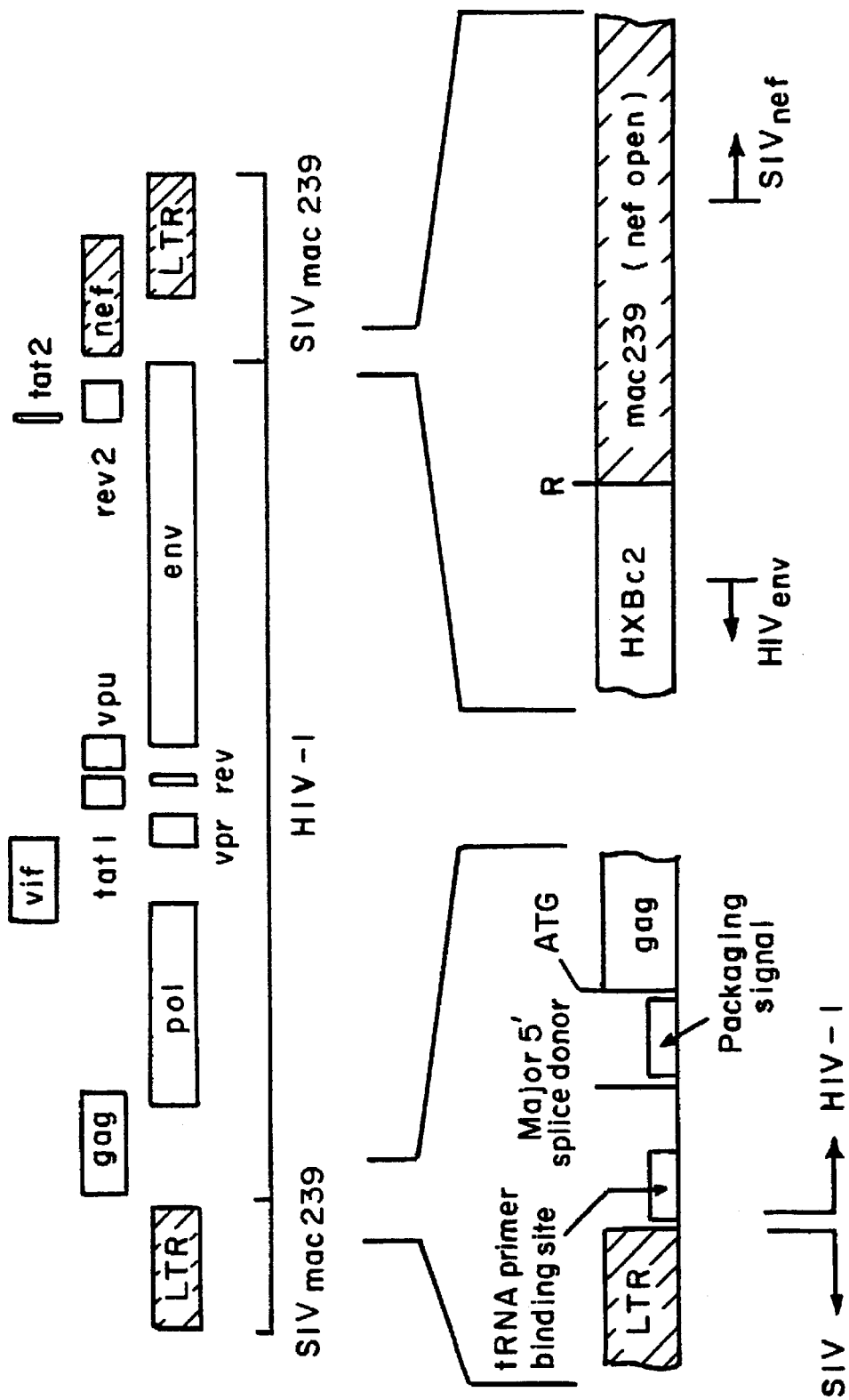
FIG. 1D is a linear schematic showing the structure of a different preferred hybrid vector.

In the preferred embodiment in which the vector encodes functional HIV-1 gag, pol, pro, vif, vpr, vpu, env, rev, and tat proteins, and functional SIV nef protein, there are two junctions between the HIV-1 and SIV sequences. The 5' junction joins the SIV 5' LTR and the HIV-1 sequences immediately 5' to the tRNA primer binding site. The 3' junction joins the HIV-1 sequences immediately 3' to the HIV-1 env gene to the SIV sequences that include the nef gene and 3' LTR, and would be similar to that shown in FIG. 1C. FIG. 1D is a schematic showing this vector. In this Figure all the genes in the HIV-1 segment are active and will express functional protein.

In another preferred embodiment, the vector of the present invention comprises a DNA sequence corresponding to a sufficient number of nucleotides of the SIV genome to encode functional SIV gag, pro and pol structural proteins and functional vif, vpx, vpr and nef SIV regulatory proteins. The vector also contains a sufficient number of nucleotides corresponding to the SIV LTRs. These sequences are referred to as the SIV segment. The vector also contains a DNA segment corresponding to a sufficient number of nucleotides of the HIV-1 genome to express a functional HIV-1 envelope glycoprotein and at least the tat and rev HIV-1 regulatory proteins. This segment is called the HIV-1 sequence. In a preferred embodiment, the HIV-1 sequence also contains a sufficient number of nucleotides corresponding to the HIV-1 genome to express a functional vpu regulatory protein.

The HIV genomes including SIV and HIV-1 have been extensively mapped for a variety of different strains. Thus, the skilled artisan can readily prepare nucleotide sequences that will contain a sufficient number of nucleotides to encode such functional proteins. Although there is strain to strain variation, both SIV (including HIV-2) and HIV-1 show a significant functional sequence homology, which phenomenon is well known to the person of ordinary skill in the art. Thus, the skilled artisan can readily prepare sequences that will produce functional proteins. For example, although the HXBc2 provirus does not encode a functional vpu protein, it is known that by inserting an AUG codon just upstream, and in frame with the vpu open reading frame, e.g., at HIV-1HXBc2 nucleotide 5541, one can express a functional vpu protein. Other alterations can be made to produce functional proteins. A functional structural protein is one that when expressed assembles into a virion in conjunction with gag and performs a particular replicarive function. A functional regulatory protein is one that will exhibit in vivo or in vitro a known functional property. For example, the tat protein stimulates viral LTR to express viral RNA. As used herein, the term corresponding to include conservative deletions, alterations and additions, e.g., coding for a change from one amino acid to another that will preserve the function of the protein.

These sequences can be prepared by a variety of means well known to the skilled artisan. For example, one can use SIV proviruses and HIV proviruses to generate the sequence. Another method involves the synthesis of the nucleotides based on known sequences. Preferably, the nucleotides that correspond to a sufficient number of nucleotides to encode a functional protein is the gene for the protein.

We have also found that it is preferable that the vectors do not contain nucleotide sequences corresponding to too many multiple splice acceptors. For example, it is preferred that the vector does not contain nucleotide sequences corresponding to the SIV tat splice acceptor, the SIV rev splice acceptor and the HIV-1 tat splice acceptor. Preferably, the vector does not have a sufficient number of sequences corresponding to the HIV-1 tat splice acceptor.

In one preferred embodiment, the vector can be derived by using an infectious SIV provirus such as $SIV_{mac}239$ nef (virus) (gag+, pro+, pol+ vif+, vpx+, vpr+, tat+, rev+, env+, nef+) [Kestler, H., et al., *Science* 248:1109–1112 (1990); and Kestler, H. W., et al., *Cell* 65:651–662 (1991), both of which are incorporated herein by reference], although other SIV strains can be used and, an HIV-1 provirus such as, BRU, ELI, Mal, HXBc2, BH10, BH5, ADA etc., for example, in the following discussion the HXBc2 strain (gag+, pro+, pol+ vif+, vpr–, tat+, rev+, vpu–, env+, nef–) [Fisher, et al., *Nature* 316:262–266 (1985), which is incorporated herein by reference] will be used as exemplary, but any of the other HIV-1 strains can readily be used instead.

The vector contains a 5' portion and a 3' portion. The 5' portion of the vector has nucleotides corresponding to the SIV genome. FIG. 1 is a linear schematic showing the vector. The white boxes correspond to HIV-1 specific sequences, whereas the darkened correspond to SIV specific sequences. Genes that are defective in these strains, meaning they will not encode a functional protein, are denoted within astericks. The 5' $SIV_{mac}$/HIV-1 junction at the SphI site (S) and the 3' HIV-1/$SIV_{mac}$ junction at the RsrII site (R) are shown. The stippled 3' end of vpr of the hybrid vector represents sequences derived from the HIV-1 portion of the chimera that reconstitutes the $SIV_{mac}$239 vpr. Thus, the 5' portion of the vector comprises a sequence corresponding to a 5' SIV-LTR, SIV gag gene, SIV pol gene, SIV vif gene, SIV vpx and a chimeric gene derived from the 5' and 3' portions that corresponds to the SIV vpr.

The 3' portion of the vector comprises tat, rev and env sequence derived from HIV-1 isolates and the nef and 3' LTR sequence derived from SIV. FIG. 1B shows the details of a 5' $SIV_{mac}$/HIV-1 junction near the SphI site (S) for a number of different vectors. The details of segments from SHIV-1 are represented by SEQ ID NOS:1, 2, 3 and 4; SHIV-2 are represented by SEQ ID NOS:1, 5 and 6; SHIV-3 are represented by SEQ ID NOS:7, 2, 3 and 4; and SHIV-4 are represented by SEQ ID NOS:7, 5 and 6. The positions of the splice acceptors (S. A.) for the $SIV_{mac}$ tat and rev messages and for the HIV-1 tat messages are shown above the figures, with the $SIV_{mac}$ tat initiation codon, $SIV_{mac}$ vpr stop codon and the HIV-1 tat initiation codon underlined and labeled with arrows below. The astericks denote sequence identity and the dot represents sequences not shown. The horizontal bars represent sequence deletions. The X marks the position of an Xba I site in 2 of the vectors designated SHIV-3 and SHIV-4. FIG. 1C shows the details of the 3' HIV-1/$SIV_{mac}$239 (nef open) junction near the Rsr II site (R) and is represented by SEQ ID NO:8. The stop codon for the HIV-1 env and the initiation codon for the $SIV_{mac}$nef are underlined and labeled with arrows.

In one embodiment the 5' proviral clones can be obtained from the known p239 SpSp 5' plasmid, which consists entirely of sequences from the $SIV_{mac}$239 clone. Such sequences can be cloned into another plasmid. For example, the pBs (+) plasmid (Stratagene) modified to contain a unique ClaI site in the polylinker region. 5' portions corresponding to the 5' portion of the vector can be readily prepared from other SIV strains using known plasmids by a similar methodology. This clone can be used to generate different vectors referred to herein as SHIV viruses. For example, one containing the $SIV_{mac}$239 tat splice acceptor and tat initiation codon. One can use known methods to eliminate or alter such sequences. For example, by use of site-directed mutagenesis, you can create a modified clone in which the tat splice acceptor and tat initiation codon are modified as shown in FIG. 1B. See, particularly in FIG. 1B, the clones labeled SHIV-3 and SHIV-4 (SEQ ID NO:7). Other alterations to the nucleic acid sequences to modify them to result in a "modified sequence" are permissible as long as they do not inactivate the protein produced by the sequences.

The 3' portion of these vectors preferably contains the HIV-1 tat gene, the HIV-1 rev gene, and the HIV-env gene. In one preferred embodiment, this portion also contains an HIV-1 vpu gene. The tat, rev and env genes can be derived from any HIV-1 strain, for example, HXBc2. The 3' portion also preferably contains the SIV nef gene and the SIV LTR. Preferably, the SIV LTR is the 3' SIV LTR.

The nef sequence, preferably the nef gene, encodes a functional nef protein. The sufficient number of nucleotides needed to encode such a functional protein can readily be determined by the person of ordinary skill in the art in light of the present disclosure. Thus, for example, when one uses, as the SIV sequence, DNA which corresponds to $SIV_{mac}$239, the skilled artisan would know that one would have to modify the nef sequence to produce a functional nef protein. For example, one would use site-directed mutagenesis to change the 93rd codon of nef from a stop (TAA) to a, for example, Glu (GAA) codon, which will encode a functional nef protein. [Kestler, H. W., et al., *Cell* 65:651–662 (1991)]. In vitro functional nef protein can be determined by its ability in primary lymphocytes to enhance replication at least two fold.

The junction between the HIV-1 sequence and the $SIV_{mac}$ sequence in the 3' portion of the vector can be formed by any methods of ligating the two segment together. For example, by using a Rsr II site, which can be created by means well known in the art, such as, for example, site-directed mutagenesis in both the HIV-1 and SIV sequence. For example, with HIV-1HXBc2 strain and $SIV_{mac}$239, (SEQ ID NO:8) and FIG. 1C shows details of a junction near the Rsr II site (R).

As aforesaid, it is preferable that both the SIV tat splice acceptor sequence and the HIV tat splice acceptor sequences are not present. This can also be accomplished by means well known in the art. For example, using a unique SphI site, which can be introduced by site-directed mutagenesis into the HIV region upstream of the HIV-1 tat gene, one can position the site such that the HIV-1 tat splice acceptor sequences will either be included or excluded from the 3' portion of the sequence. Vectors which include the HIV-1 tat splice acceptor are shown in FIG. 1B and referred to as SHIV-1 and SHIV-3 chimeric viruses, while the vectors which lack the HIV-1 tat splice acceptor were designated as SHIV-2 and SHIV-4 viruses.

It is also important that the vector encodes a functional vpr protein. Since the last few codons of the $SIV_{mac}$ vpr gene are located 3' to the natural Sph I site in the 5' proviral clone, these codons were supplied in the vector by modification of the 3' portion near the introduced Sph I site. Thus, the vpr reading frame is restored upon ligation of the 5' and 3' sequences at the Sph I site. See, FIG. 1.

In one embodiment the vector can also contain a sufficient number of nucleotides encoding a protein other than from HIV-1 or SIV, for example, a marker protein such as CAT. However, because the inclusion of such additional DNA can slow down replication efficiency, its inclusion is dependent upon the particular use of the vector.

The vector can be transfected into cells by standard techniques. For example, the vector can be digested with Sph I and other restriction enzymes that recognize the flanking sequences, such as Cla I for the 5' portion and Xho I for the 3' section. The fragments containing the 5' and 3' sequences are ligated. The ligation reaction is mixed with cells in a standard medium such as 1 milliliter of serum-free RPMI 1640 and DEAE-dextran. The cell-DNA suspension is then incubated at appropriate conditions, for example, 37°, for a sufficient time for transfection, for example, 1 hour. The cells are then washed and resuspended in the medium.

Virus production in these cells is monitored periodically, for example, every three to four days by a standard assay, such as reverse transcriptase assay. For example, as taught by Rho, H., et al., *Virology* 112:355–360 (1981).

These infected cells can then be used to obtain virus which can be used to infect an animal. One can infect an animal, for example, a macaque, by standard techniques, such as inoculation intravenously with virus stock. Monkeys such as rhesus monkeys and macaques are the preferred test animal. However, other mammals susceptable to SIV infection, preferably primates can be used. One would also mock infect with a mock virus or SIV or HIV-1 to monitor disease progression. Following inoculation of the animal, such as a cynomolgus monkey, PMBCs can be isolated and cultured and the level of a marker protein, such as, for example, SIV gag p27 antigen in culture assayed by known means, such as that described by Miller, M. D., et al, *J. Immunol.* 144:122–128 (1990). The vectors described herein not only will infect the test animal, but also should result in the establishment of disease.

Another means of infecting monkeys with the vector is to inject the vector DNA intramuscularly into the animals. (Letvin et al., *Nature*).

These vectors create replication competent SIV-HIV-1 hybrid viruses that will express HIV-1 envelope glycoproteins as well as the HIV-1 regulatory proteins tat and rev in a variety of primate species, such as monkeys or apes. The rate of appearance of virus in the peripheral blood mononuclear cells of infected monkeys using the present vector is comparable to that of the rate of infection with a pathogenic strain of SIV, such as $SIV_{mac}239$. Based upon the results thus far obtained, it is expected that these viruses express functional vif, vpx, vpr and nef regulatory proteins of SIV and the tat and rev regulatory proteins of HIV-1. When an HIV-1 vpu gene, which will express a functional vpu gene product is present, it is expected to express functional vpu protein. Accordingly, these results indicate that the restriction of HIV replication in monkeys, such as cynomolgus monkeys is not due to determinants in the tat, rev or envelope proteins.

Furthermore, we believe that the high level of replication we have obtained with our vectors is a result of their containing functional vpr and nef gene products. Although Shibata, et al. has described a chimeric $SIV_{mac}$/HIV-1 virus, that expresses the HIV-1 envelope glycoprotein, this virus is defective for both vpr and nef. *J. Virol.* 65:3514–3520 (1991). Shibata also teaches that neither vpr or nef is necessary for replication. We believe, however, that a virus produced according to the method of Shibata is not as efficient as that described here for both replication and infection in animal models. Preliminary reports indicate that the Shibata et al. virus establishes only a low level, transient infection in monkeys (M. Hayami, personal communication).

It is preferable not to have an HIV-1 tat splice acceptor site in the vector. It appears that the presence of the HIV-1 tat splice acceptor near the 5' $SIV_{mac}$/HIV-1 junction results in inefficient expression of viral genes.

The present vectors, which can create hybrid viruses, that can infect a wide range of primates such as monkeys, permit a wide variety of tests. For example, one can screen for the ability of vaccines to induce protective immune responses in monkeys to infection by the hybrid virus which will permit a method for teaching the efficacy against viruses with HIV-1 envelope glycoproteins. This model can also be used to evaluate the ability of polyclonal and monoclonal antibodies to inhibit HIV-1 envelope function in animals, as well as to evaluate therapeutics designed to inhibit any of the HIV-1, tat, rev, env or vpu functions. These vectors permit the development of AIDS-like disease and further enhance the ability to allow dissection of the pathogenic potential of envelope glycoprotein variance, allowing assessment of therapeutic efficacy using clinical end points, which further allow evaluation of the ability of vaccine candidates to modify disease induction. This is addressed in more detail below.

Whether an animal has become infected with the hybrid virus can be determined by monitoring for signs of the disease by standard techniques, such as looking at clinical status. This can be done by standard means well known to the skilled artisan, for example, careful physical examinations on the inoculated animal at periodic intervals, e.g., bi-weekly, monthly, bimonthly. The animals can be monitored to see if there is any weight loss as well as development of lymphadenopathy and splenic and/or hepatic enlargement.

At periodic intervals blood can be drawn and the virus isolated and cultivated by standard means. Absolute peripheral blood lymphocytes subset counts can be assessed at such periodic intervals to determine onset of infection. Humoral response to the virus can also be assessed. For example, one can determine antibody titer to the virus by, for example, indirect immunofluorescence and/or the presence of antibodies to the various proteins, such as anti-envelope and anti-core antibody response, for example, by radioimmuno-precipitation and gel electrophoresis.

As previously discussed, this model will permit the ability to more fully understand the role of variation within the HIV envelope glycoprotein. In HIV-1-infected humans most of the neutralizing antibodies elicited early in infection are directed against the V3 loop of the gp120 glycoprotein. Neutralizing antibodies generated later in the course of infection are directed against more conserved epitopes among the HIV-1 isolates. For example, antibodies against the mostly discontinuous epitopes that overlap the CD4 binding site. The present model provides the ability to determine whether similar progression of immune responses will occur in animals infected with the hybrid virus. In contrast to the case with humans, the monkeys will only be infected with one HIV-1 envelope strain. Thus, one can assess whether similar progression of immune responses occur in these animals by standard techniques such as collecting serum. In animals that generate antibodies to the HIV-1 envelope glycoprotein, the presence and titer of the neutralizing antibodies will be determined. One can use virus neutralization assays. One can also assess the strain restriction of neutralizing antibodies by using an env gene complementation assay. See for example, Helseth, E., et al., *J. Virol.* 64:2416–2420 (1990). Such an assay will allow a precise estimate of the activity of a serum or monoclonal antibody to neutralize a single round of virus entry into a variety of target cells. In one method, an env-defective HIV provirus encoding a marker such as the CAT enzyme will be co-transfected into a susceptible cell line, e.g. COS-1 cells, with a plasmid expressing the env gene of interest. One would use env genes from any of the various HIV-1 strains. Virons containing only mutant glycoproteins are then harvested from the COS-1 cell supernatants 48 hours after transfection, filtered, incubated with serum or antibody preparation and then placed on the target cells. CAT assays are done on the cells at a periodic time after infection, for example, two days. One can also prepare the claimed vector with different env sequences to determine the effect of different envelope glycoproteins on disease in animals. Thus, one could use a vector containing the env gene having a sequence of, for example, BRU, ELI, BH10, etc.

The env complementation assay can also be employed to address V3 loop specificity and whether there is any strain restriction of any of the observed neutralizing antibodies in infected animal serum. For example, neutralizing activity of the serum against, for instance, the parental HXBc2 envelope glycoproteins can be assessed. A replication-competent HXBc2 mutant envelope glycoprotein with a change of proline 313 at the tip of the V3 loop to serine can be tested in parrallel. By making changes such as this, one has been able to dramatically reduce the sensitivity of HXBc2 virus to neutralization by a variety of anti-V3 loop monoclonal antibodies. The ratio of the ability of an animal serum to neutralize recombinant virus with the change in proline 313 to the ability to neutralize viruses with the parental HXBc2 envelope glycoprotein indicates the percentage of neutralizing activity in the serum that is directed against the tip of the V3 loop. A second approach that can be used to assess the effect of V3-directed antibodies to the neutralizing activity of infected animal serum, involves competition with peptides corresponding in sequence to the V3 loop. The competing V3 loop peptide must correspond in sequence to that of the envelope glycoprotein being utilized in the env complementation assay. Increasing concentrations of peptide, as well as a control peptide of scrambled sequence will be added to the animal serum prior to incubation with the recombinant virus. Peptides will also be incubated with neutralizing human monoclonal antibodies directed against epitopes outside of the V3 loop to permit the ability to control for non-specific effects of the peptide on the assay. The ratio of neutralizing activity in the presence of the highest concentration of peptide to the neutralizing activity observed in the absence of peptide represents the fraction of the patient activity attributable to the V3 loop.

These vectors also provide a method for determining the specific epitopes of the envelope glycoproteins recognized by cytotoxic T-lymphocytes (CTL). In humans, single amino acid changes in the HIV-1 envelope glycoprotein can result in loss of recognition. However, with patient sera, it is not practical to generate a series of overlapping peptides representing an envelope glycoprotein of the predominant HIV isolate to allow a meaningful mapping of the env epitopes recognized by CTL in that individual. Because these animals will be infected with a single envelope species, it is possible to assess the evolution and epitope specificity of HIV-1 env-specific CTL. For example, one can change the env sequence in the vector generating the virus that will be used to infect the animal and assess its effect.

Furthermore, since we are starting with a single virus, by periodically assaying the envelope glycoprotein as well as the infected RNA and DNA, for example, by polymerase chain reaction (PCR), one can determine the occurrence, if any, of variation for virus in the animal. In one embodiment, virus is isolated periodically, for example, every month and tested. Tests can be, for example, the ability of serum from each time point to neutralize viruses taken at different times from the same animal. Where neutralization escape is observed, one can look at the sequence variation in the gene by the use of polymerase chain application. The results can be compared with samples of the gene obtained prior to seroconversion.

A method for evaluating the effect of the HIV-1 envelope glycoprotein and tropism is also possible with these vectors.

For example, by employing two different envelope genes one can evaluate the effect of the different envelope genes both in vivo and in vitro. In one preferred embodiment, one can construct chimeric genes, such that one will obtain different gp120 and gp41 ectodomain while retaining similar transmembrane and intracytoplasmic tails. For example, the ADA envelope glycoproteins have been shown to infect primary human macrophages, but not to infect or form syncytia with established T-cell lines. [Westervelt, P., et al. Proc. Natl. Acad. Sci. U.S.A. 88:3097–3101 (1991)]. Whereas the HXBc2 envelope glycoprotein are typical of those variants that allow efficient infection of established T-cell lines, induce the formation of synctytia, establish high multimeric affinity for CD4 and exhibit sensitivity to soluble CD4. [Sodroski, J. et al., Nature 322:470–474 (1986); Thali, M. et al., J. Virol. 65:5008–5012 (1991)]. By inserting the Kpn I to Bsm I fragment of the ADA env gene into the analagous site of the HXBc2 env gene one will obtain a chimeric envelope sequence which will result in essentially the entire gp120 and gp41 ectodomains derived from ADA and the transmembrane region and the intracytoplasmic tail derived from HXBc2. Using one of the vectors containing such a gene, hybrid virus can be produced which expresses this envelope glycoproteins. These proteins have been shown to retain the replicative and tropic phenotype associated with the complete ADA glycoprotein. These viruses can be tested in vitro for ability to replicate on PBMCs and primary macrophages of human and cynomolgus monkeys. Preferably, one would use primary macrophage derived from human peripheral blood. Preferably, the cynomolgus monkey macrophages can be derived from bronchoalveolar lavages and from bone marrow as described by Ringler, D., et al., J. Med. Primatol. 18:217–226 (1989) and Watanabe, M., et al., Nature 337:267–270 (1989). One will use standard means to determine whether the HIV ADA envelope glycoproteins allow entry into the cynomolgus monkey macrophages, e.g., tissue culture observation for syncytria. In another embodiment animal models are used, one injects half the animal models with hybrid virus containing the ADA envelope chimeric genes and half with virus containing HXBc2 envelope genes. The monkeys are then evaluated to determine the differences between the two groups. For example, by looking at viral tropism, neutralizing antibody responses, envelope sequence drift, viral burden and pathogenicity, This can be done by standard techiques. One can also look at early and late antibody responses in these animals to determine whether the different envelope glycoproteins result in qualitative difference in anti-envelope antibody responses generated. Furthermore, PCR-based approaches, such as discussed above, can also be used to determine the evolution of env-sequence variation in these two groups of animals.

One can also use the animal model to assess the role of various regulatory proteins. For example, one can insert functional vpu proteins into the HIV segment and compare the replication of viruses that express vpu protein against those viruses that don't express such protein (Control virus) in vivo and in vitro. For example, the vpu positive and control virus can be analyzed in the animal models, for example, cynomolgus monkeys for relative rates of replication, potential differences in the ratio of cell-associated to cell-free virus in the peripheral blood and for pathogenicity.

One can also use the animal model to more fully understand the effect of the virus on various organs and body systems. For example, intracranial injections, and screening animals permits the ability to study the effect of the virus on the central nervous system.

One sensitive indicator of a positive role of a gene in virus replication is the tendency to revert minimally altered but non-functional genes back to wild-type sequences. Accordingly, we will also use a vector which contains such a vpu gene, i.e. one where only a few nucleotide changes are required to allow expression of a fully functional vpu product. These changes can be determined by a variety of means, e.g., using vpu-antibody to look for vpu protein or by using PCR amplification. Any reverted vpu sequences can then be recloned into infectious chimeric proviruses.

One can also screen potential compounds for their therapeutic effect on these viruses. Thus, one can administer potential vaccines to the animals and then try to inoculate with the hybrid viruses produced by these vectors, wait and determine whether infection occurs. This assessment can be made by any of the means discussed above. The standard technique would be to take a control group that is inoculated with a mock vaccine and a similar group that is inoculated with the actual vaccine at various concentrations. Thereafter, one determines whether infection occurs.

Similarly, one can screen infected animals for therapeutic compounds. One inoculates the hybrid virus-infected animals with the test compound and a control (placebo) under standard conditions and screens to determine whether or not the animals show any differences from the baseline control, which has been mock treated. One looks at the same criteria as one looked at before, such as virus titer, pathogenicity, weight loss or gain, antibody production, etc.

The drug to be tested or the virus when inoculated can be delivered by any of a number of means, for example, it can be administered by parenteral injection (intramuscular I.M.), intraperitoneal (I.P.), intravenous (I.V.), intracranial (I.C.) or subcutaneous (S.C.)), oral or other routes of administration well known in the art. Parenteral injection is typically preferred. For example, I.C. would be used when looking at drugs effecting the central nervous system. The amount to be tested or inoculated will usually be in the range of about 0.1 mg to about 10 mg/kg of body weight.

The material can be administered in any means convenient, for example, it can be mixed with an inert carrier, such as sucrose, lactose or starch. It can be in the form of tablets, capsules and pills. For parental administration, it will typically be injected in a sterile aqueous or non-aqueous solution, suspensions or emulsion in association with a pharmaceutically-acceptable parenteral carrier.

In addition to using the animal models to test compounds and vaccines, one can also screen the adjuvants that are being used with, for example, the vaccines or therapeutic to determine the most appropriate adjuvant. This can be done in a manner similar to that described above for screening therapeutic compounds. In one preferred embodiment, one can test the desired therapeutic or vaccine with a variety of different adjuvants to see the different effects, if any, of the adjuvants.

The present invention is further illustrated by the following examples. These examples are provided to aid in the understanding of the invention and are not to be construed as a limitation, thereof.

Plasmid constructions

The vectors producing the hybrid viruses (sometimes also referred to as chimeric viruses) were constructed using the infectious, pathogenic $SIV_{mac}$239 (nef-open) virus (gag+, pro+, pol+, vif+, vpx+, vpr+, tat+, rev+, env+, nef+) [Kestler, H., et al., *Science* 248:1109–1112 (1990); Kestler III, H. W., *Cell* 65:651–662 (1991)] and the HXBc2 HIV-1 virus (gag+, pro+, pol+, vif+, vpr−, tat+, rev+, vpu−, env+, nef−) [Fisher, A., et al., *Nature* 316:262–266 (1985)]. All four chimeric viruses (designated SHIV) used in this study express the gag, pro, pol, vif, vpr and nef proteins of $SIV_{mac}$239 (nef open) and the tat, rev, and env proteins of HIV-1 (HXBc2).

Each chimeric provirus clone was propagated in *E. coli* using two plasmids, one containing the 5' half of the provirus and one containing the 3' half of the provirus. The 5' proviral clones, derived from the p239 SpSp 5' plasmid [Kestler, H., et al., *Science* 248,supra], consisted entirely of sequences from the $SIV_{mac}$239 clone. The sequences from the 5' cellular flanking sequences to the unique Sph I site in the $SIV_{mac}$239 genome were cloned into a pBS(+) plasmid (Stratagene) modified to contain a unique Cla I site in the polylinker region. This 5' clone, which was used to generate the SHIV-1 and SHIV-2 chimeric viruses, contains the $SIV_{mac}$239 tat splice acceptor and tat iniation codon. Site-directed mutagenesis was used to create a modified 5' clone in which the $SIV_{mac}$ tat splice acceptor and tat initiation codon were modified (FIG. 1B). The details of the 5' $SIV_{mac}$/HIV-1 junction near the Sph I site (S) are shown for each of the SHIV chimeric viruses. The positions of the splice acceptors (S.A.) for the $SIV_{mac}$ tat and rev messages and for the HIV-1 tat message are shown above the figure, with the $SIV_{mac}$ tat initiation codon, $SIV_{mac}$vpr stop codon and HIV-1 tat initiation codon underlined and labeled with arrows below. The astericks denote sequence identify and the dots represent sequences not shown. The horizontal bars represent sequence deletions. The X marks the position of Xba I site in the SHIV-3 and SHIV-4 sequences (SEQ ID NO:7). This modified 5' clone was used to generate the SHIV-3 and SHIV-4 chimeric viruses.

The 3' proviral clones consisted of tat, rev and env sequences derived from the HXBc2 HIV-1 isolate and the nef and 3' LTR sequences derived from the $SIV_{mac}$239 (nef open) isolate [Kestler III, H. W., et al., *Cell* 65,supra]. In the $SIV_{mac}$239 (nef open) variant, the 93rd codon of nef is changed from a stop (TAA) to a Glu (GAA) codon, allowing production of a functional nef protein. [Kestler III, H. W., et al., *Cell* 65supra.

The HIV/$SIV_{mac}$ junction in the 3' proviral clones was formed by ligating the HIV-1 and $SIV_{mac}$ segments using the Rsr II site, which was created by site-directed mutagenesis in both the HIV-1 and $SIV_{mac}$239 (nef open) sequences. See, FIG. 1C.

To allow efficient ligation of the 5' and 3' proviral halves, a unique Sph I site was introduced by site-directed mutagenesis into the HIV-1 region upstream of the HIV-1 tat gene. This Sph I site was positioned such that the HIV-1 tat splice acceptor sequences would be either included in or excluded from the 3' proviral clones. The 3' clone that included the HIV-1 tat splice acceptor was used to generate the SHIV-1 and SHIV-3 chimeric viruses, while the 3' clone lacking the HIV-1 tat splice acceptor was used to generate the SHIV-2 and SHIV-4 viruses (FIG. 1A). The genetic organization of the HIV-1 (HXBc2), $SIV_{mac}$239 (nef open), or SHIV chimeric viruses is shown, with HIV-1 or $SIV_{mac}$-specific sequences designated as white or black boxes, respectively. Genes that are defective in the strains utilized are denoted with an asterick. The 5' $SIV_{mac}$/HIV-1 junction at the Sph I site (S) and the 3' HIV-1/$SIV_{mac}$ junction at the Rsr II site (R) are shown. The stippled 3' end of vpr of the SHIV virus represents sequences derived from the HIV-1 portion of the chimera that reconstitute the $SIV_{mac}$239 vpr. Also since the last few codons of the $SIV_{mac}$ vpr gene are located 3' to the natural Sph I site in the 5' proviral clone, these codons were supplied by modification of the 3' proviral clone near the introduced Sph I site. Thus, the vpr reading frame would be restored upon ligation of the 5' and 3' proviral clones at the Sph I site (FIG. 1B).

Transfection of CEMx174 Cells With Chimeric Proviruses For transfection, 5 micrograms of the 5' and 3' proviral clones were digested with Sph I and other restriction enzymes that recognize the flanking sequences (Cla I for the 5' proviral clone and Xho I for the 3' proviral clone). The fragments containing the 5' and 3' proviral sequences were ligated. The ligation reaction was then mixed with $3 \times 10^6$ CEMX174 cells suspended in 1 ml of serum-free RPMI 1640 and 500 ug/ml DEAE-dextran. The cell-DNA suspension was incubated at 37° C. for one hour, after which the cells were washed with serum-free medium and resuspended in 10 ml RPMI 1640 with 10% fetal calf serum.

Reverse Transcriptase Assays

Virus production in transfected or infected cultures was monitored every 3-4 days by reverse transcriptase assays as described, using 1.5 ml of cell-free supernatant [Rho, H., et al., Virology 112:355-360 (1981)]. After removing supernatants for reverse transcriptase assays, cells were resuspended in a sufficient amount of fresh medium to maintain the cell density between $10^5$ and $10^6$ cells/ml.

Infection of Cultured Monkey PBMCs

Typically, $2-4 \times 10^7$ PBMCs were isolated from 15–30 ml whole blood from cynomolgus monkeys. Cells were isolated using Ficoll-Paque (Pharmacia) and resuspended in RPMI 1640 supplemented with 10% fetal calf serum and either phytohemagglutinin (PHA-C) (Boehringer-Mannheim) or concanavalin A (Con A, type IV, Sigma) at 5 ug/ml. Three to five days following PHA-C or Con A stimulation, the cells were washed and resuspended in RPMI 1640 with 10% fetal calf serum and 10 U/ml interleukin-2 (human recombinant, Boehringer-Mannheim). Two days later, PBMCs were infected with $1 \times 10^5$ reverse transcriptase units of virus derived from transfected CEMx174 cells. Three days after infection, PBMCs were washed and resuspended in fresh medium.

Reverse transcriptase measurements in cell supernatants were made on days 4, 6, 9 and 13 following infection.

Preparation Of Virus Stocks and $TCID_{50}$ Determination

Virus stocks for animal inoculation were prepared in cynomolgus monkey PBMCs and frozen as cell-free supernatants without additives at −70° C. The virus titer was determined by incubation 100 ul of thawed stocks, either undiluted or as 10-fold serial dilutions, in quadruplicate with $1 \times 10^5$ CEMx174 cells in 1 ml of medium. When cultures became confluent, cells were diluted $\frac{1}{10}$. The wells were scored for the presence of syncytia after 2 weeks, and the $TCID_{50}$ in the virus stock calculated as described [Jawetz, E., et al., pp. 371-385 in Review of Medical Microbiology, 14th ed. Lange Medical Publications, Los Altos, Calif.].

Immunoprecipitation of Infected Cultures

Approximately $2 \times 10^6$ CEMx174 cells were infected with HIV-1 (HXBc2 strain), $SIV_{mac}239$ (nef open), or chimeric viruses. The cultures were labeled overnight with $^{35}S$-cysteine 1-2 days prior to the peak of syncytium formation, and cell lysates were precipitated either with serum from an HIV-1 infected AIDS patient or from an $SIV_{mac}$-infected rhesus macaque as described [Thali, M., et al., J. Virol. 65:6188–6193 (1991)].

Inoculation of Cynomolgus Monkeys With Chimeric Virus

Two male and two female cynomolgus monkeys (M. fascicularis) were incoculated intravenously with 1 ml of virus stock containing $7 \times 10^3$ $TCID_{50}$ of the SHIV-4 chimeric virus.

Virus Isolation From Inoculated Cynomolgus Monkeys

At two and four weeks following inoculation of cynomolgus monkeys, CD8-depleted, Con A-stimulated PBMCs were cultured from each animal and the level of $SIV_{mac}$ gag p27 antigen in culture supernatants assessed as described [Miller, M. D., et al., J. Immunol. 144:122-128 (1990)]. Culture supernatants positive for viral antigen were used to infect CEMx174 cells, which were labeled and used for immunoprecipitation as described above.

Chimeric Viruses

As discussed above, the sequences used for the construction were derived from the pHXBc2 DNA, a clone prepared from the IIIB strain of HIV-1 [Fisher, A., et al., Nature 316,supra], and the p239 SpSp 5' and p239 SpE3'/nef-open plasmids derived from the $SIV_{mac}239$ strain of virus. Injection of cynomolgus or rhesus monkeys with either purified $SIV_{mac}239$ viral DNA or virus derived from this DNA has resulted in both high levels of viremia and an AIDS-like disease [Kestler, H., et al., Science 248,supra; Kestler, III, H. W., et al., Cell 65,supra; Letvin, N., et al., Nature 349:573 (1991)].

Construction of the appropriate chimeric molecules was complicated by significant differences in the regulatory genes of the two viruses as well as the complex genetic organization of the primate immunodeficiency viruses [Desrosiers, R. C., et al., AIDS Res. Hum. Retro. 5:465–473 (1989); Guyader, M., et al., Nature 326:662–669 (1987); Viglianti, G. A., et al., J. Virol. 62:4523–4532 (1988)]. Both HIV-1 and $SIV_{mac}$ encode the regulatory genes vif, vpr, tat, rev and nef. The regulatory vpu is specified only by HIV-1 [Cohen, E. A., et al., Nature 344:532–534 (1988); Klimkait, T., et al., J. Virol. 64:621–629 (1990); Strebel, K., et al., J. Virol. 63:3784–3791 (1989); Strebel, K., et al., Science 241:1221–1223 (1988); Terwilliger, E. F., et al., Proc Nat'l Acad. Sci. U.S.A. 86:5163–5167 (1989); Willey, R., et al., J. Virol. 66:226–234 (1992)], whereas vpx is found only in HIV-2 or SIV [Henderson, L. E., et al., Science 241:199–201 (1988); Hu, W., et al., Virology 173:624–630 (1989); Kappes, J. C., et al., Virology 184:197–209 (1991)]. By replacing the tat, rev, and env sequences of $SIV_{mac}239$ by the corresponding sequences of HXB2, the resultant virus contains the LTR gag, pol, vif, vpx, vpr, and nef of $SIV_{mac}$ and tat, rev, and env of HIV-1.

The initial chimeric virus made, designated SHIV-1 (SIV-HIV-chimeric virus-1), contains two tat splice acceptor sequences. The 5' tat splice acceptor sequence is of $SIV_{mac}$ origin (SEQ ID NO:1) whereas the 3' tat acceptor sequence is derived from HIV-1 sequences (SEQ ID NO:3). To minimize the possibility that the presence of two closely spaced splice acceptor sites might interfere with one another, derivatives of SHIV-1 were made that contain only the $SIV_{mac}$ splice acceptor site (SHIV-2) (SEQ ID NOS:1 and 6), only the HIV-1 splice acceptor site (SHIV-3)(SEQ ID NOS:7 and 3) or neither splice acceptor site (SHIV-4) (SEQ ID NOS:7 and 6) (FIG. 1B). In the virus that lacks both tat splice acceptors, it is believed that the $SIV_{mac}$ rev acceptor substitutes for the tat acceptor.

Replication Of Chimeric Viruses In Culture

The parenal $SIV_{mac}239$ virus replicates well in the human CD4$^+$ B/T cell hybrid line CEMx174 [Salter, R. D., et al., Immunogenetics 21:235–246 (1985)]. CEMx174 cells were transfected with the parental $SIV_{mac}239$ as well as SHIV recombinant DNAs. Virus replication was monitored by measurement of the amount of the viral DNA polymerase (reverse transcriptase) released into the culture medium.

Figure 2A:
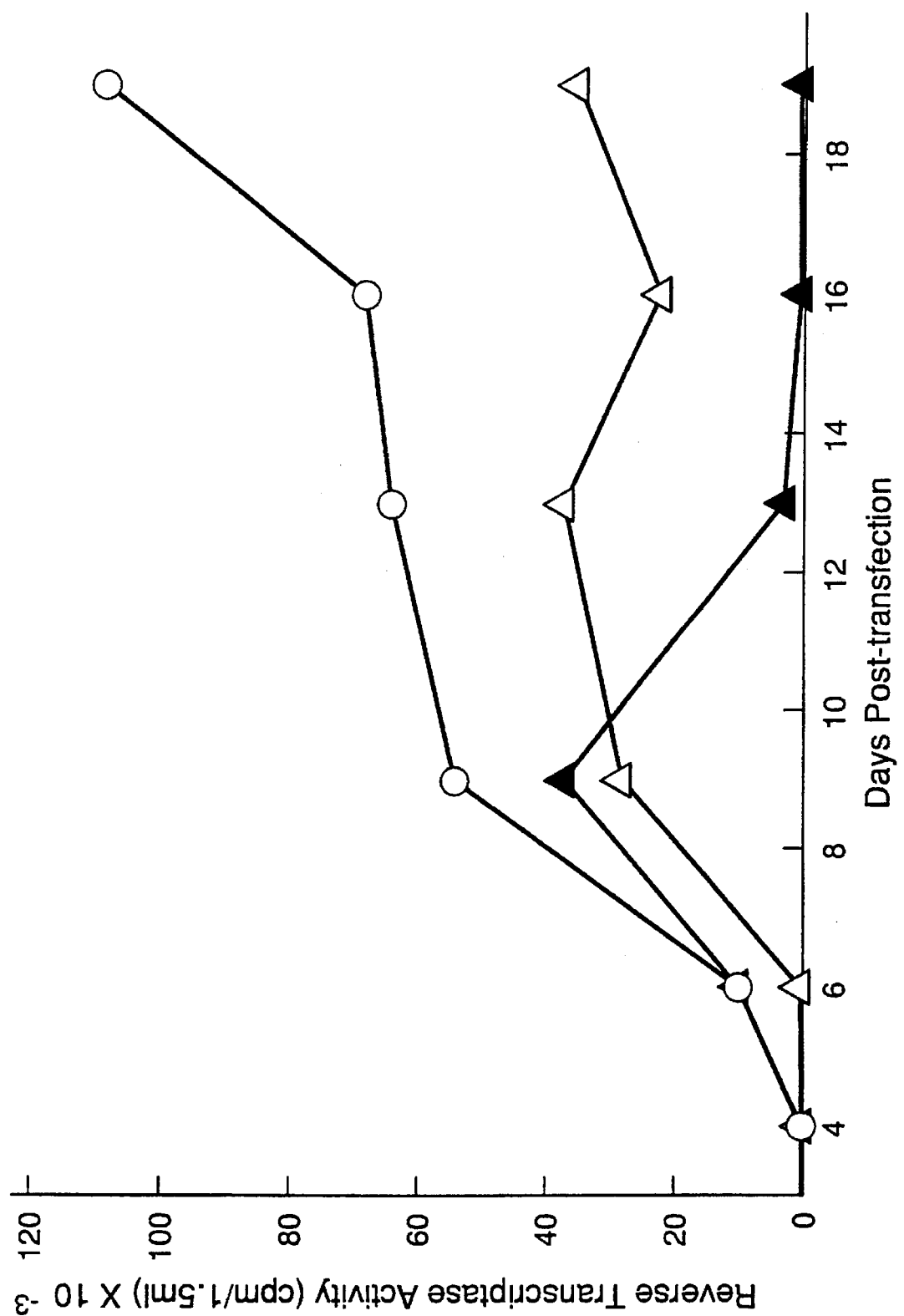
FIG. 2 is a graph showing the replication of the parental $SIV_{mac}239$ DNA (o) and the SHIV-2 ( ) and SHIV-4 ( ) DNAs (FIG. 2A) and the replication of the SHIV-1( ) and SHIV-3 ( ) DNAs (FIG. 2B) in CEMx174 lymphocytes.
Figure 2B:
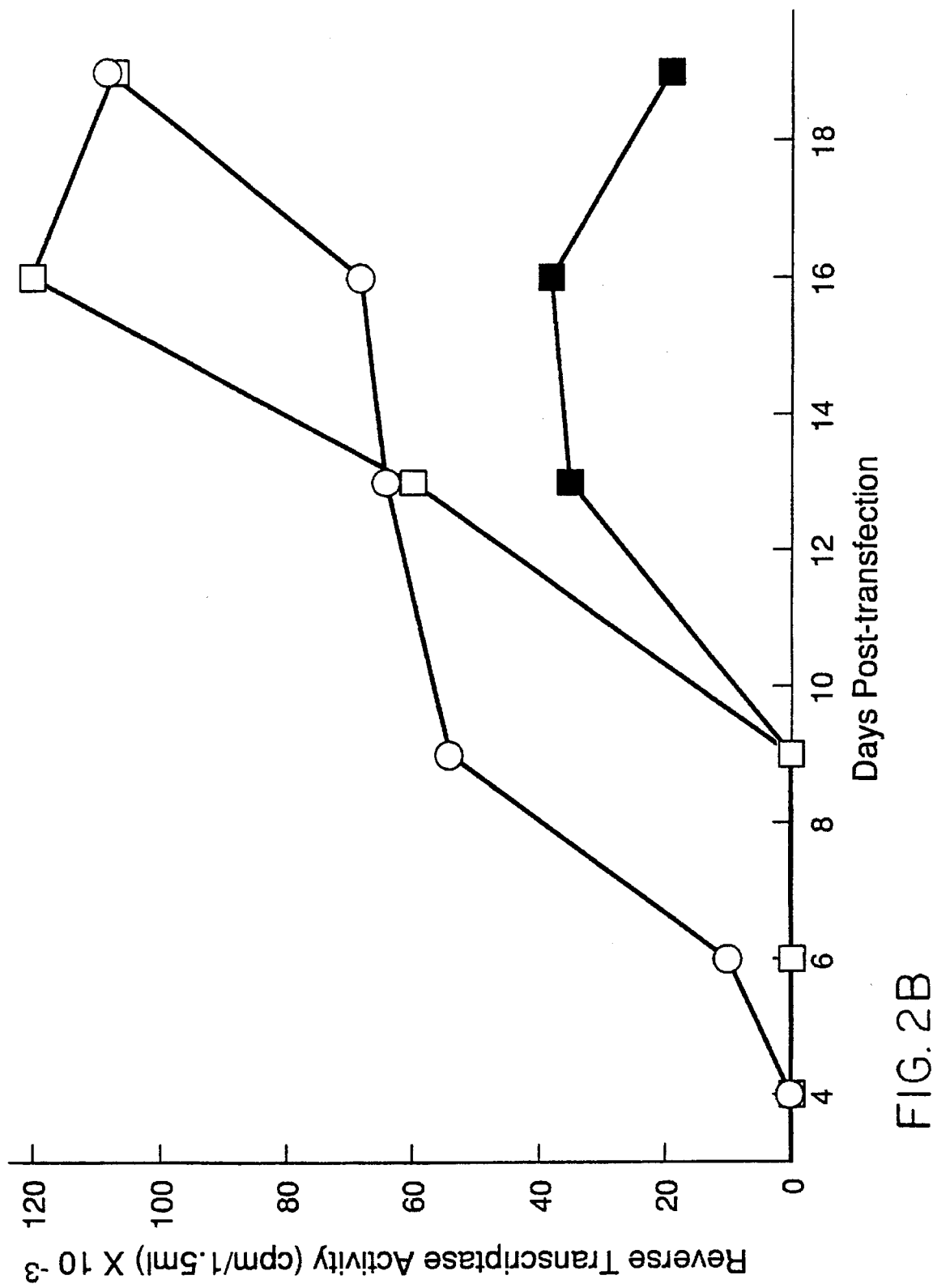

The data of FIG. 2 shows that virus is produced from cultures that are transfected with all five DNAs. However, significant differences in the rate of appearance of reverse transcriptase in the medium was noted using different DNAs. Significant virus replication was evident by nine days post-transfection in cultures treated with either the parental $SIV_{mac}239$ DNA (◯) or the SHIV-2 (▲) or SHIV-4 DNAs (△) (FIG. 2A). Detectable levels of reverse transcriptase were not present in the cultures transfected with SHIV-1 or SHIV-3 DNAs until day 13 post-transfection (FIG. 2B). The relative delay in appearance of virus in the supernatant of cultures transfected with SHIV-1 (■) or SHIV-3 (□) as compared to those transfected with $SIV_{mac}239$, SHIV-2 or SHIV-4 DNAs was observed in several independent experiments. Despite this reproducible delay, the rates of replication of all four chimeric viruses were indistinguishable when similar amounts of virus harvested from the supernatant fluids of the transfected cultures were used to reinfect CEMx174 cells (data not shown).

The ability of SHIV-2 and SHIV-4 viruses to initiate infection in primary peripheral blood mononuclear cells (PBMCs) derived from cynomolgus monkeys was examined. For these experiments the $SIV_{mac}239$, SHIV-2 and SHIV-4 viruses harvested from the supernatant fluids of tranfected CEMx174 cells were incubated with PHA-1 or Con A-activated monkey PBMCs. Three days after infection with these viruses, the PBMCs were washed and resuspended in fresh medium. Virus replication was measured by detection of reverse transcriptase activity in culture supernatant fluids.

TABLE 1

Reverse Transcriptase Activity (cpm/1.5 ml × $10^{-3}$) in Supernatants of Cynomolgus Monkey PBMCs

| Virus | Days After Infection | | | |
|---|---|---|---|---|
| | 4 | 6 | 9 | 13 |
| $SIV_{mac}239$, (nef-open) | 33 | 45 | 30 | 61 |
| SHIV-2 | 96 | 82 | 41 | 28 |
| SHIV-4 | 57 | 76 | 17 | 34 |

The data of Table 1 show that all three viruses replicated well in cultures of PBMCs derived from cynomolgus monkeys. The rate of replication and amount of virus produced upon infection of the monkey PBMCs with either the SHIV-2 or SHIV-4 virus was similar to that obtained upon infection of the culture with $SIV_{mac}239$.

Chimeric Nature Of The Recombinant Viruses

The SHIV chimeras produce gag and pol products of $SIV_{mac}$ and env proteins of HIV-1. The viral gag proteins of HIV-1 and $SIV_{mac}239$ can be distinguished by mobility differences on SDS-polyacrylamide gels, following precipitation with sera from HIV-1 infected humans of $SiV_{mac}$-infected monkeys. Such sera contain antibodies that cross-react with gag but not with env proteins [Kanki, P., et al., Science 228:1199–1201 (1985)].

Viruses harvested from the supernatant fluids of infected PBMC cultures were used to infect CEMx174 cells. As controls, CEMx174 cells were infected with $SIV_{mac}239$ (nef open) and HIV-1 (HXBc2) viruses. The infected cells were labeled with $^{35}$S-cysteine, lysed, and the viral proteins precipitated with serum from an HIV-1-infected AIDS patient or serum from a $SIV_{mac}$-infected macaque. The precipitates were analyzed on SDS-polyacrylamide gels.

Figure 3A:
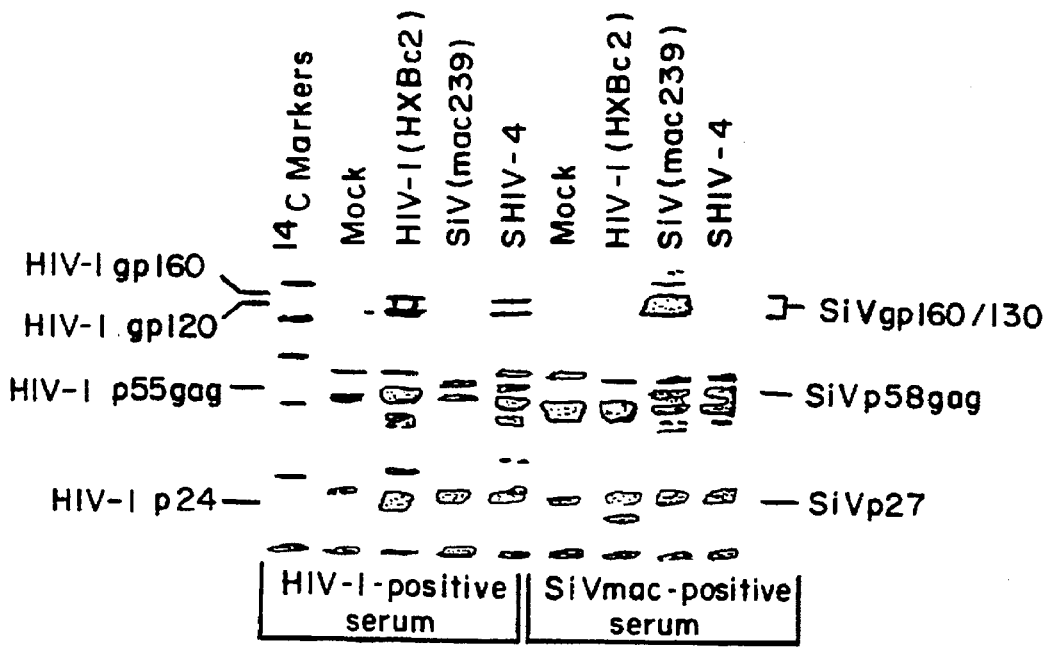
FIG. 3A are autoradiographs of CEMx174 cells infected with $SIV_{mac}$ 239 virus or a virus produced by one of the vectors of the present invention from cynomolgus monkey PBMCs.

The data of FIG. 3A show that, both the human and monkey sera recognize gag proteins of the parental HIV-1 and SIV viruses. CEMx174 cells were infected with $SIV_{mac}239$ (nef open) virus or SHIV-4 virus that had been produced from cynomolgus monkey PBMCs. In parallel, CEMx174 cells were infected with HIV-1 (HXBc2 strain). Infected CEMx174 cells and uninfected (Mock) controls were labeled, lysed, and precipitated either with HIV-1 positive human serum or serum from a $SIV_{mac}$-infected macaque. The position of the HIV-1 and $SIV_{mac}$-specific gag and env products are marked. The molecular weight markers shown are 200, 96, 69, 46 and 30 kD. These proteins can be distinguished from one another by electrophoretic mobility of both the capsid proteins (HIV-1 p24 and $SIV_{mac}$p27) and the gag precursor proteins (HIV-1 p55 and $SIV_{mac}$p58). The HIV-1 serum recognizes the gp160 and gp120 env glycoproteins present in CEMx174 cells infected with HIV-1 but not the env proteins of cells infected with $SIV_{mac}239$. The anti-$SIV_{mac}$ serum recognizes the gp160 and gp130 env proteins present in cells infected with $SIV_{mac}239$ but not with the HIV-1 virus.

In these experiments the gag proteins present in cells infected with the SHIV-4 virus exhibited the electrophoretic mobility characteristic of $SIV_{mac}$ capsid proteins. The env proteins of these extracts were recognized by the anti-HIV-1 but not the anti-$SIV_{mac}$ serum. The electrophoretic mobilities of the env proteins present in cells infected with the SHIV-4 virus corresponded to those expected for the envelope glycoproteins of HIV-1. These experiments confirm that the SHIV-4 virus is chimeric and produces the gag proteins of $SIV_{mac}$ and the env proteins of HIV-1.

Infection Of Cynomolgus Monkeys

SHIV-4 virus was grown in cynomolgus monkey PBMCs as described above. The titer of virus produced in the PBMCs was determined using CEMx174 cells as targets. An amount of virus equivalent to $7 \times 10^3$ TCID$_{50}$ units was injected intravenously into four cynomolgus monkeys that were seronegative for $SIV_{mac}$. At two and four weeks post-infection PBMCs were isolated from the inoculated monkeys. The lymphocyte population was depleted for CD8$^+$ T cells and activated with Con A as described previously [Miller, M. D., et al, J. Immunol. 144:122–128 (1990)]. Virus was detectable by both p27 gag protein released into the culture fluid and by the formation of syncytia in activated PBMC cultures of all four monkeys at two and four weeks post-infection (data not shown).

Figure 3B:
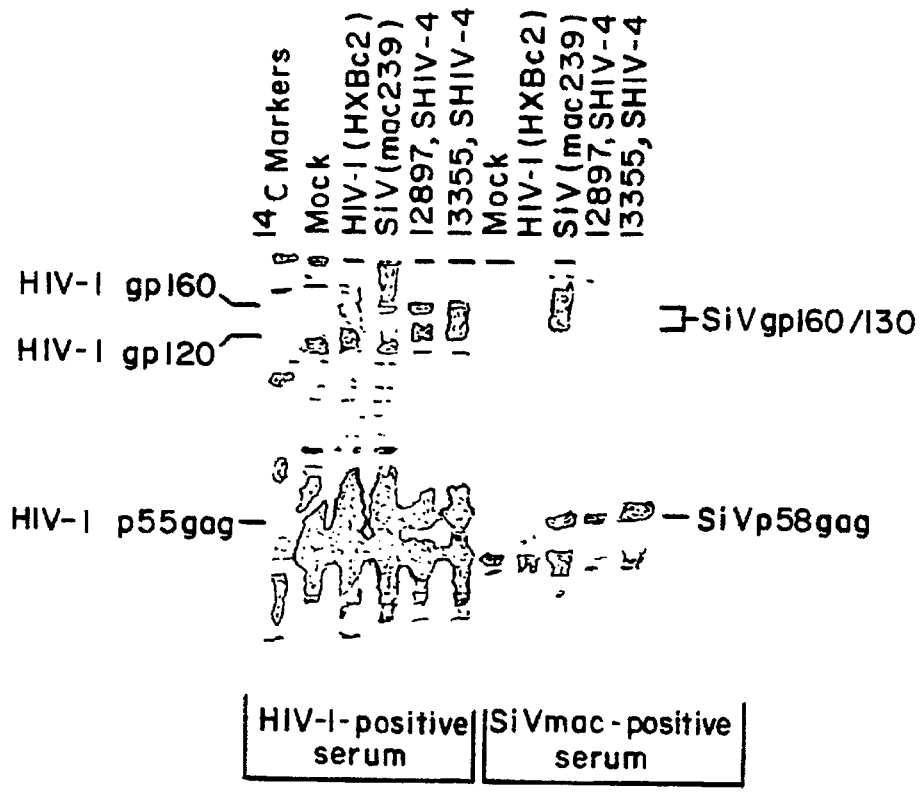
FIG. 3B are autoradiographs showing CEMx174 cells infected with virus from one of the vectors isolated from cynomolgus macaques at 2 weeks post inoculation.

The culture fluid obtained from the activated PBMCs of the four monkeys was used to infect CEMx174 cells with the SHIV-4 virus isolated therefrom (numbers 12897 and 13355) at two weeks post-inoculation. In parallel, CEMx174 cells were infected with HIV-1 (HXBc2 strain) or $SIV_{mac}239$ (nef open) viruses or mock-infected. The cells were labeled with $^{35}$S-cysteine, lysed and precipitated either with anti-HIV-1 and anti-$SIV_{mac}$ serum as described above. The molecular weight markers shown are 200, 96, 69 and 46 KD. The viruses isolated from all four animals encoded gag precursor proteins that exhibited a mobility identical to that of the $SIV_{mac}$ gag precursor protein, and encoded env proteins that were precipitated with HIV-1-positive but not $SIV_{mac}$-positive serum (FIG. 3B and data not shown).

It is evident that those skilled in the art, given the benefit of the foregoing disclosure, may make numerous modifications thereof and departures from the specific embodiments described herein, without departing from the inventive concepts and the present invention to be limited solely by the scope and spirit of the appended claims.

We claim:

1. A vector comprising a 5' DNA segment and a 3' DNA segment, wherein
   (a) the 5' DNA segment contains a sufficient number of nucleotides corresponding to an SIV or HIV-2 genome to encode functional SIV or HIV-2 gag protein, pol protein, pro protein, vif protein and vpx protein, and has an SIV or HIV-2 LTR, and, (b) the 3' DNA segment contains a sufficient number of nucleotides corresponding to at least one HIV-1 genome to encode a functional HIV-1 env protein, HIV-1 tat protein, and HIV-1 rev protein and a sufficient number of nucleotides corresponding to an SIV or HIV-2 genome to encode a functional nef protein and has an SIV or HIV-2 LTR, and, (c) the vector contains a sufficient number of nucleotides corresponding to an SIV or HIV-2 genome to encode a functional SIV or HIV-2 vpr protein.

2. The vector of claim 1 wherein the 3' segments also contains a sufficient number of nucleotides corresponding to the HIV-1 genome to encode a functional HIV-1 vpu protein.

3. The vector of claim 1 wherein the SIV genome is the $SIV_{mac}$, $SIV_{agm}$, or $SIV_{MND}$.

4. The vector of claim 1 wherein the sufficient number of nucleotides needed to encode a functional protein corresponds to the gene for that protein.

5. The vector of claim 1 wherein the sufficient number of nucleotides encoding the HIV-1 envelope protein correspond to a different strain of HIV-1 than the sufficient number of HIV-1 nucleotides encoding the HIV-1 tat and rev proteins.

6. The vector of claim 1 wherein the sufficient number of nucleotides encoding the functional HIV-1 env protein comprises a chimeric HIV-1 genome.

7. The vector of claim 1 wherein the vector does not contain a nucleotide sequence corresponding to a HIV-1 tat splice aceptor.

8. The vector of claim 1 or 3 wherein the HIV-1 genome is selected from the group of HIV-1 strains consisting of Eli, Bru, Mal, HXBc2, BH10, BH5 and ADA.

9. The vector of claim 3 wherein the HIV-1 genome is HXBc2.

10. The vector of claim 8 wherein the SIV genome is $SIV_{mac}$.

11. A vector comprising a sufficient number of nucleotides corresponding to an SIV 5' LTR, a SIV 3' LTR for initiation of RNA synthesis and a sufficient number of nucleotides to encode a functional SIV nef protein, a functional HIV-1 env protein, a functional HIV-1 tat protein, a functional HIV-1 rev protein, a functional SIV or HIV-1 gag protein, a functional SIV or HIV-1 pol protein, a functional SIV or HIV-1 pro protein, and a functional SIV or HIV-1 vif protein.

12. The vector of claim 11 which also encodes a functional SIV vpx protein.

13. The vector of claim 11 which encodes HIV-1 gag protein, HIV-1 pol protein, HIV-1 pro protein and HIV-1 vif protein.

14. The vector of claim 11 or 12 which also enclodes a functional HIV-1 vpu protein.

15. The vector of claim 14 which also encodes functional HIV-1 vpu protein.

16. The vector of claim 15 which also encodes functional SIV vpx protein.

17. A vector comprising:

(a) nucleotides corresponding to an SIV genome to encode and express SIV gag+, pol+, vif+, nef+ and vpx+ proteins, and (b) nucleotides corresponding to an HIV genome to encode and express HIV tat+, rev+ and env+ protein, wherein the vector only contains one tat splice acceptor sequence, and, wherein the resulting proteins are assembled into a replication and infection competent chimeric virus.

18. The vector of claim 17, wherein the vector further comprises nucleotides to encode and express the SIV vpr+ protein.

19. The vector of claim 18, wherein the vector further comprises nucleotides corresponding to an HIV genome to encode and express an HIV vpu+ protein.

* * * * *

UNITED STATES PATENT AND TRADEMARK OFFICE
CERTIFICATE OF CORRECTION

PATENT NO : 5,654,195
DATED : August 5, 1997
INVENTOR(S) : Joseph Sodroski, et al.

It is certified that error appears in the above-identified patent and that said Letters Patent is hereby corrected as shown below:

Col. 1, before line 4, insert -- -The above invention was made, in part, with support from NIH Grant No. AI29333 and the United States Government has certain rights thereto.- -

Signed and Sealed this

Twentieth Day of July, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:1:

TATAATAGAC ATGGAGACAC CCTTGAGA                                      28

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:2:

AGAAGCATGC TCTAGGCTGC AGGAATTC                                      28

( 2 ) INFORMATION FOR SEQ ID NO:3:

( i ) SEQUENCE CHARACTERISTICS:
        ( A ) LENGTH: 9 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:3:

TTTTCAGAA                                                                                            9

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:4:

AGGAGAGCAA GAAATGGAG                                                         19

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:5:

AGAAGCATGC TGTAG                                                                  15

( 2 ) INFORMATION FOR SEQ ID NO:6:

( i ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown (x i) SEQUENCE DESCRIPTION: SEQ ID NO:6:

AGCAAGAAAT GGAG 14

(2) INFORMATION FOR SEQ ID NO:7:

(i) SEQUENCE CHARACTERISTICS:
      (A) LENGTH: 28 base pairs
      (B) TYPE: nucleic acid
      (C) STRANDEDNESS: unknown
      (D) TOPOLOGY: unknown (x i) SEQUENCE DESCRIPTION: SEQ ID NO:7:

TATAATCGTC ACGGAGACAC TCTAGAGA 28

(2) INFORMATION FOR SEQ ID NO:8:

(i) SEQUENCE CHARACTERISTICS:
      (A) LENGTH: 30 base pairs
      (B) TYPE: nucleic acid
      (C) STRANDEDNESS: unknown
      (D) TOPOLOGY: unknown (x i) SEQUENCE DESCRIPTION: SEQ ID NO:8:

CTATAAGACG GACCGACCTA CAATATGGGT 30